United States Patent [19]
Roche

[11] 3,941,566
[45] Mar. 2, 1976

[54] DEVICE FOR DETERMINING CARBON ACTIVITY THROUGH PRESSURE

[75] Inventor: Michael F. Roche, Lombard, Ill.

[73] Assignee: The United States of America as represented by the United States Energy Research and Development Administration, Washington, D.C.

[22] Filed: Jan. 10, 1975

[21] Appl. No.: 540,182

[52] U.S. Cl. ................. 23/230 R; 23/253 R; 73/19
[51] Int. Cl.² ........................................... G01N 7/12
[58] Field of Search..... 73/19, 23; 23/230 R, 232 R, 23/253 R, 254 R; 55/158

[56] References Cited
UNITED STATES PATENTS

| | | | |
|---|---|---|---|
| 3,060,726 | 10/1962 | Weber | 73/19 |
| 3,451,256 | 6/1969 | Kolodney | 73/23 |
| 3,679,551 | 6/1972 | Kolodney | 204/1 T |
| 3,681,026 | 8/1972 | Holden | 73/19 X |
| 3,797,299 | 3/1974 | Nelson et al. | 73/19 |
| 3,843,419 | 10/1974 | Schmidt | 23/230 R |

Primary Examiner—Richard C. Queisser
Assistant Examiner—Stephen A. Kreitman
Attorney, Agent, or Firm—Dean E. Carlson; Arthur A. Churm; Hugh W. Glenn

[57] ABSTRACT

A hollow iron capsule of annular shape having an interior layer of $Fe_{0.947}O$ and a near absolute internal vacuum is submersed within a molten metal with the inner chamber of the capsule connected to a pressure sensor. Carbon present in the molten metal diffuses through the capsule wall and reacts with the $Fe_{0.947}O$ layer to generate a $CO_2$—CO gas mixture within the internal chamber. The total absolute pressure of the gas measured by the pressure sensor is directly proportional to the carbon activity of the molten metal.

6 Claims, 3 Drawing Figures

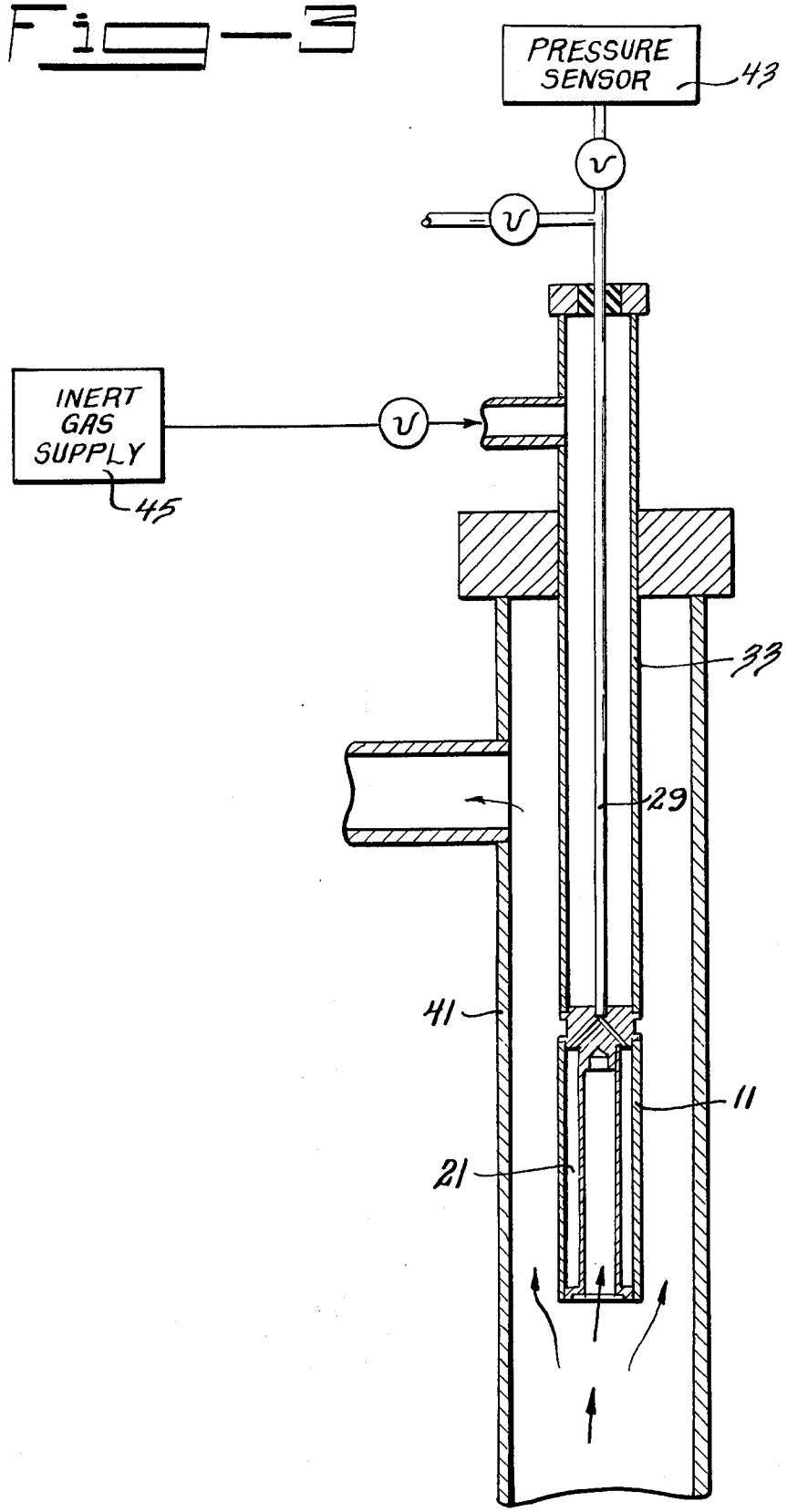

DEVICE FOR DETERMINING CARBON ACTIVITY THROUGH PRESSURE

CONTRACTUAL ORIGIN OF THE INVENTION

The invention described herein was made in the course of, or under, a contract with the UNITED STATES ATOMIC ENERGY COMMISSION.

BACKGROUND OF THE INVENTION

The present invention relates to devices and methods for measuring the carbon activity of fluids containing carbon. It has particular application in the measurement of carbon activity in liquid metals such as sodium used as coolant in nuclear reactors or other systems.

The carburization and decarburization of stainless steels in contact with high-temperature liquid metals such as sodium can produce detrimental effects on mechanical properties. Therefore the determination of carbon activity within liquid-metal coolant of reactor systems can play an important role in determining the useful life of the reactor components.

Various methods have previously been employed to determine carbon content or carbon activity of a liquid-metal system. Some have involved the analysis of samples, either of the liquid metal itself or of solid metallic tabs exposed to the liquid metal. For more or less continuous monitoring, sampling techniques of this type require the frequent taking of samples and the required in-laboratory analysis which can be tedious and time-consuming.

Various meters for installation within lines or vessels containing liquid metal have included types that are based on the measurement of carbon diffusion rate through a metallic barrier. Since such meters require a flow of carbon out of the molten metal to be monitored, the measurement is influenced by the liquid-metal flow rate and by the form of dissolved carbon in the liquid metal. Thus, a simple measurement of the carbon activity is not obtained. Other systems involving electrochemical and pressure measurements have been quite complicated and have required precise and frequent calibration for accurate results. Impurities within the operating materials of such systems have produced additional difficulties in calibration and the selection of suitable range.

SUMMARY OF THE INVENTION

Therefore, in view of the prior art devices and techniques for measuring carbon activity within a fluid, it is an object of the present invention to provide an improved device for continuously and accurately monitoring the carbon activity of a fluid through pressure measurements.

It is also an object to provide a method of monitoring carbon activity within a fluid which can be performed by periodic pressure readings without the requirement of frequent recalibration or resetting of range.

It is a further object to provide a method and device for determining carbon activity of a fluid based on an absolute pressure measurement.

In accordance with the present invention, a device for measuring the carbon activity of a fluid is provided. The device comprises a capsule having iron walls defining an internal chamber and means for measuring the pressure within that chamber. Prior to employing the device as a carbon meter, a layer of wustite, $Fe_{0.947}O$, is deposited on the interior surfaces of the capsule and the capsule is evacuated. (Wustite is the iron oxide in equilibrium with iron at 700°C.) On submersing the evacuated capsule within a fluid of unknown carbon activity, carbon from the fluid diffuses through the capsule wall and reacts with the wustite layer to form carbon monoxide and carbon dioxide gas. When an equilibrium gas mixture with respect to the wustite layer and iron capsule walls has been formed within the capsule, the ratio of carbon dioxide to carbon monoxide will always equal a constant and the total pressure will be proportional to the carbon activity in the capsule wall. Since at equilibrium the net carbon diffusion through the capsule wall is zero, carbon activity in this wall is equal to that within the fluid being monitored. The proportional relationship of total pressure to carbon activity is achieved by fixing the oxygen activity within the chamber through the iron-wustite equilibrium and by producing all of the carbon monoxide and carbon dioxide gas through reaction of diffused carbon with the wustite layer.

The wustite layer is formed on the interior surfaces of the capsule by filling the capsule with a mixture of carbon monoxide and carbon dioxide gas in the proportion that is formed in the carbon wustite reaction, that is, approximately 60% carbon monoxide and 40% carbon dioxide. The total pressure of this filling gas is adjusted to be substantially above that equivalent to the highest carbon activity expected to be monitored. The capsule is then submersed in a liquid metal of extremely low carbon activity such that carbon formed from the reaction of CO and $CO_2$ with iron will diffuse through the capsule walls into the liquid metal. The second reaction product, wustite, is deposited on the interior capsule walls and will remain to be employed in the determination of carbon activity of other, unknown fluids.

Other more specific aspects of the invention include the use of an annular internal chamber within the capsule to permit both internal and external contact with the liquid to be monitored. This configuration increases the surface area to unit volume ratio and accordingly the sensitivity of the device. Other improved aspects include a jacket for isolating the pressure connections between the capsule and sensor that would otherwise contact the fluid to be monitored. This prevents corrosion of the pressure connections and the establishment of other equilibria that might otherwise alter the total pressure produced by the diffused carbon and wustite layer.

BRIEF DESCRIPTION OF THE DRAWINGS

The present invention is illustrated in the accompanying drawings wherein:

FIG. 3 is a schematic showing an in-line installation of the capsule portion of FIGS. 1 and 2 coupled to the other components of a carbon meter.

DETAILED DESCRIPTION

Figure 1:
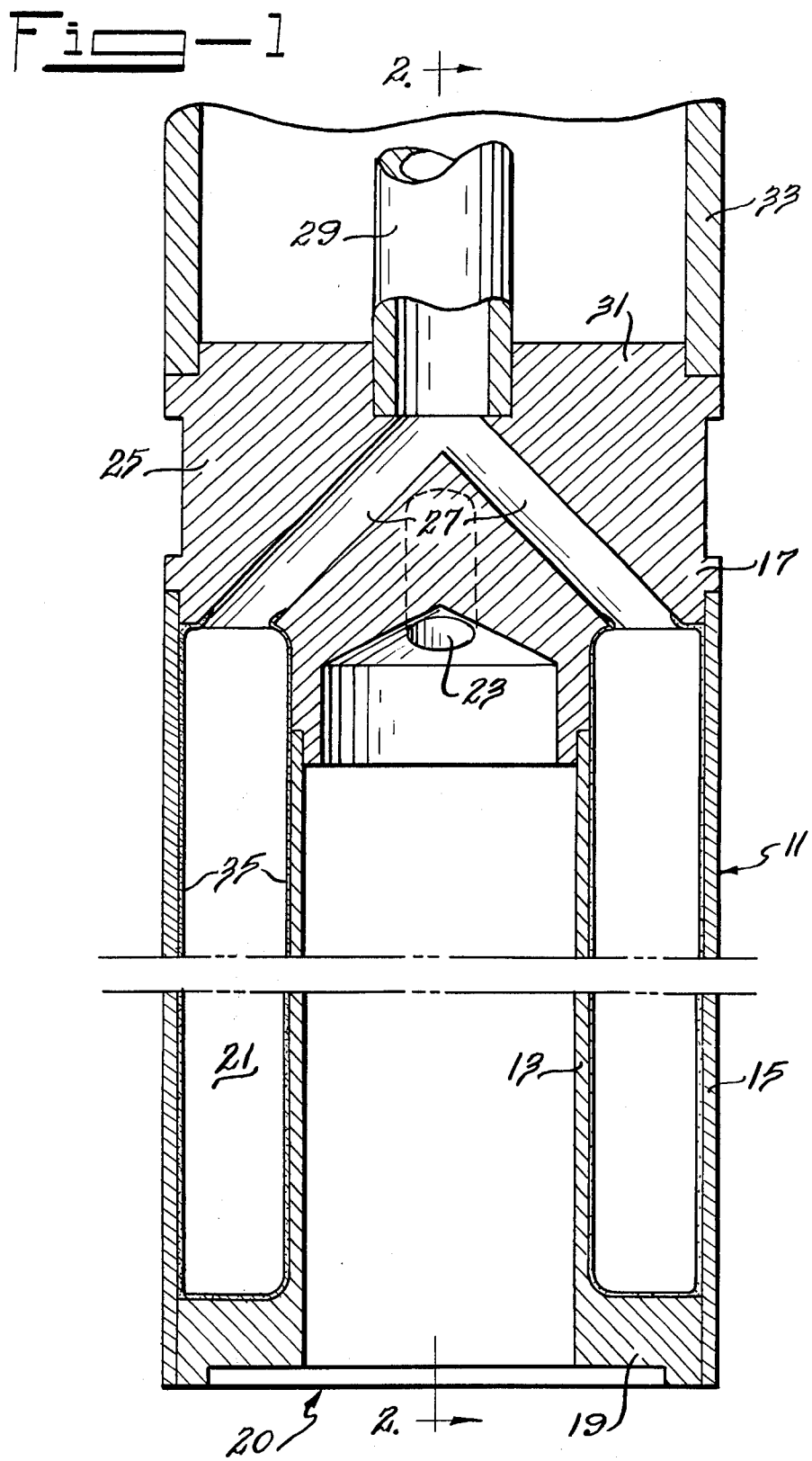
FIG. 1 is an elevation view in cross section of a capsule portion of a meter used to determine carbon activity of a fluid.
Figure 2:
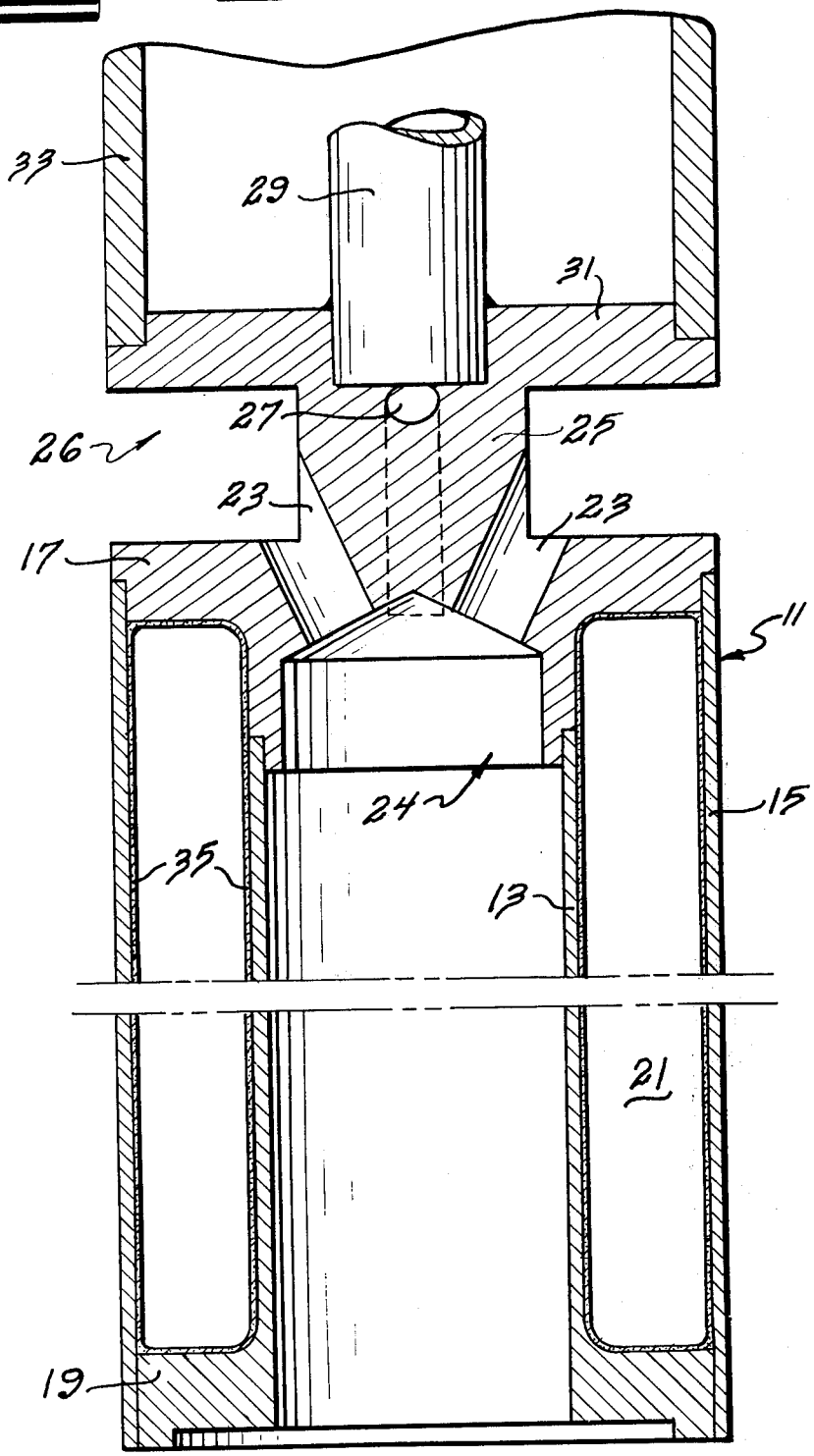
FIG. 2 is a cross section of the capsule portion of FIG. 1 taken at right angles thereto.

Referring now to FIGS. 1 and 2 where a preferred embodiment of the capsule portion of the carbon meter of the present invention is shown. The lower portion of the meter is shown as an annular capsule 11 formed of inner 13 and outer 15 concentric tubes with circular closures 17 and 19 over the upper and lower ends of the tubes. This structure defines an annular internal chamber 21 within capsule 11.

The lower end closure 19 is of a generally flat annular shape, shown integral in construction with the lower end of tube 13 and having a central opening 20 for admitting a flow of the process fluid to be monitored into the passageway of tube 13. Upper end closure 17 extends over the diameters of both the inner and outer tubes 13 and 15 and is the lower part of a connector block 25 which couples the tubes to a tubular jacket 33 surrounding a central transmission tube 29. Connector block 25 includes an axial opening 24 that branches into diverging passageways 23 into open slots 26 on opposite sides and in the central vertical region of block 25. These connecting passageways permit escape of process fluid flow entering tube 13 at its lower opening 20.

A second set of passageways 27 converge from internal chamber 21 through connector block 25 to an upper central opening adapted for the connection of the transmission tube 29. The tubular jacket 33 which encompasses tube 29 fits into the upper disk-shaped portion of connector block 25 to seal the lower end of the jacket. Jacket 33 isolates transmission tube 29 from the process fluid being monitored and can be used to contain an inert gas to protect the tube from attack by the process fluid, e.g. sodium.

Transmission tube 29 is of a nonferrous material that will not catalyze the reaction $2\,CO \rightarrow CO_2 + C$. Copper is a preferred choice as it is also generally inert to both oxygen and carbon. Where iron, iron-nickel or other iron alloys are employed for tube 29, carbon deposition (sooting) may result within the transmission tube 29 and interfere with the carbon meter operation. In a liquid sodium system operated at 700° to 750°C., this sooting problem peaks as the $CO$—$CO_2$ gas mixture cools to about 500°C. and then diminishes to negligible amounts at room temperature. Therefore it is of importance to employ copper or another material that will not catalyze the sooting reaction for transmission tubing near the high-temperature process.

Concentric tubes 13 and 15 are preferably of pure iron with less than 1/10 of 1% alloy or impurity composition. As an example, Armco (a trademark) iron tubes can be used for this purpose. The tubes are thin-walled, e.g. of about 0.01 to 0.05 cm wall thickness, to provide minimum resistance to carbon diffusion. Internal chamber 21 defined between the concentric tubes 13 and 15 is provided with an interior coating of $Fe_{0.947}O$ (wustite) 35. The equilibrium between this layer and the iron capsule walls maintains a fixed oxygen activity on the interior walls of the capsule. Details of the iron-wustite equilibrium phase diagram are given in M. Hansen, "Constitution of Binary Alloys, 2nd Ed.", McGraw-Hill Book Co., Inc., N.Y. (1958), pp. 684–688.

As carbon from the molten metal outside chamber 21 diffuses through the walls of the concentric tubes 13 and 15, the following equilibrium is established on the interior surfaces of chamber 21.

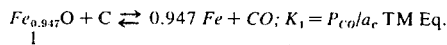

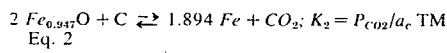

From a previous determination of these equilibrium constants ($K_1$, $K_2$) at 700°C for the above reactions, the following equations were calculated:

$$P_{CO_2}/P_{CO} = 0.578 \text{ TM Eq. 3}$$

$$P_{CO} + P_{CO_2} = 743 a_c \text{ TM Eq. 4}$$

where $P_{CO}$, $P_{CO_2}$ are the partial pressures of the corresponding gases given in Torr and $a_c$ is carbon activity. The total pressure, $P_{CO} + P_{CO_2}$, generated by these equilibria is measured by a pressure sensor means connected to internal chamber 21 by transmission tube 29 and, as shown in Eq. 4, is directly proportional to carbon activity.

The layer of $Fe_{0.947}O$ was formed on the interior surfaces of chamber 21 by filling the capsule with a mixture of carbon monoxide and carbon dioxide gas at a pressure that is substantially higher than any anticipated during use of the carbon meter. For example, about 250 Torr total pressure would be suitable for providing a wustite coating for a carbon meter to be used in measuring the carbon activity of sodium liquid metal within a stainless steel system. The composition of the carbon gas should be about 60% carbon monoxide and about 40% carbon dioxide. Such a gas mixture approximates the equilibrium gas mixture produced by carbon reaction with wustite in the above equilibria.

The capsule, having been filled with the carbon monoxide - carbon dioxide gas mixture, is submersed within a molten liquid metal such as sodium having an extremely low carbon activity to drive the equilibria of Eqs. 1 and 2 in the direction of $Fe_{0.947}O$ and carbon at the interior surfaces of chamber 21. As an example, a carbon activity of less than $10^{-2}$ corresponding to about 7 Torr equilibrium pressure should be employed within liquid sodium metal at 700°C. Such a system can be provided with molten sodium metal contained within a 304 stainless steel vessel. The capsule is maintained within liquid sodium metal of low activity until the total pressure of carbon monoxide and carbon dioxide decreases to about 1/5 of the original, e.g. about 50 Torr. Previous experience in forming wustite layers has shown that this will require about 72 hours.

After the wustite layer has been formed, the internal chamber 21 is evacuated with a suitable vacuum source or pump. For example, a pump capable of producing an absolute pressure of about $10^{-6}$ Torr will be adequate in most applications. While maintaining the high vacuum within the internal chamber, the capsule is annealed at about 700°C until no further outgassing of the wustite layer occurs. This should require about 15 minutes of annealing. The removal of residual gases eliminates the problem of contaminants which is inherent in previous gas-filled devices. Oxygen containing impurities could contribute to the reading by generation of added carbon monoxide and carbon dioxide. Inert impurities would cause a background problem by adding to the total pressure reading.

Reference is now made to FIG. 3 where the capsule 11 of applicant's carbon meter is shown installed within a liquid-metal system. The liquid-metal flow is contained within piping 41 and passes over both the inner and outer surfaces of the concentric tubes which define the internal chamber 21. Carbon contained within the liquid metal diffuses through the walls of capsule 11 to react with the wustite layer on the interior surfaces of chamber 21, producing carbon monoxide and carbon dioxide gas. When the pressure of these gases equals their equilibrium pressures, the carbon activity inside the meter is equal to that in the liquid metal being monitored, and the net diffusion flux of carbon becomes zero. The pressure is transmitted through copper tube 29 to a pressure sensor 43 where it is monitored. Jacket 33 surrounding the copper tube transmission line 29 to protect it from sodium attack extends sealingly outside the sodium piping 41. An inert gas supply 45 of such as argon gas fills jacket 33 surrounding copper tube 29 to protect it from attack by air.

Pressure sensor 43 is a pressure measurement device such as a liquid or electronic manometer capable of measuring pressure at near absolute vacuum to in excess of any pressures corresponding to carbon activities that may be encountered. One suitable sensor is an electronic manometer having a diaphragm between fixed capacitor plates. A change in total pressure deflects the diaphragm and varies the capacitance characteristics of the measurement system. Such pressure sensors are commercially available, for example, from Datametrics Inc., a division of CGS Scientific Corporation.

The carbon meter of the present invention was tested in several liquid sodium metal systems, one employing Type 200 nickel containment and the other Type 304 stainless steel. Some of the systems included cold traps, located remote from the carbon meter, which appeared to reduce carbon activity slightly. The experiments were carried out for approximately 1 week in about 700°C molten sodium metal. From the pressure measurements carbon activities were calculated and compared with activities obtained through the analysis of Fe - 12 w/o Mn tabs. The results are given in the table below.

| System | Pressure Torr | Activity from pressure | Activity from tabs |
|---|---|---|---|
| Type 200 nickel | 125.7 | 0.169 | 0.171 |
| Type 304 stainless steel | 4.9 | $6.6 \times 10^{-3}$ | $6.04 \times 10^{-3}$ |
| Type 304 stainless steel with cold trap at | | | |
| 125°C. | 1.7 | $2.3 \times 10^{-3}$ | — |
| 155°C. | — | — | $2.5 \times 10^{-3}$ |
| 155°C. | — | — | $2.9 \times 10^{-3}$ |
| 155°C. | — | — | $3.5 \times 10^{-3}$ |
| 208°C. | 2.2 | $2.9 \times 10^{-3}$ | — |

The results show good agreement between the activities determined with the pressure readings of the carbon meter of the present invention and those determined by analysis of the iron-manganese tabs. The tabs were maintained in contact with the sodium metal for the full week. They were then withdrawn, cooled, cleaned and analyzed for their carbon content by combustion anaylsis using a conventional carbon-oxygen determinator. The instrument employed was calibrated with a reference steel procured from the National Bureau of Standards (Type 335 steel with 0.1% carbon). Further details on carbon activity through tab analysis along with a description of the present invention is given in Argonne National Laboratory Report "The Determination of Carbon in Sodium by Tab Equilibrations and by Carbon Meters and the Carburization of Stainless Steel in Sodium Systems," ANL-8017, distributed February 1974. This report is hereby incorporated by reference into the present application.

It can be seen from the above that the present invention provides an accurate carbon activity meter which is capable of continuous monitoring of a system. The meter provides good sensitivity at low carbon activities from the equilibria of diffused carbon with the wustite layer on the internal surfaces of the capsule. By beginning with essentially zero absolute pressure within the chamber, all of the gas pressure is provided by this equilibria and it is seen to be proportional to the carbon activity. The essentially zero initial reference pressure and the fixed oxygen activity provided by the $Fe_{0.947}O$ and iron equilibrium therefore negates the need for frequent recalibration of the present carbon meter.

The embodiments of the invention in which an exclusive property or privilege is claimed are defined as follows:

1. A device for measuring the carbon activity of a fluid containing carbon comprising: a capsule adapted to contact a fluid of unknown carbon activity having an internal chamber with walls of a material including iron, an iron oxide layer covering the interior surfaces of said capsule walls, pressure-sensor means for measuring the absolute pressure within said chamber, copper tubing interconnecting said internal chamber of said capsule and said means for determining the absolute pressure of said internal chamber and an outer jacket sealingly surrounding said copper tubing over a portion of its length immediately adjacent to said capsule in order to prevent contact of said fluid with said copper tubing.

2. The device of claim 1 wherein said internal chamber is of annular shape defined by inner and outer, concentric iron tubes with upper and lower end closures extending laterally between said tubes, said end closures including openings communicating with the inner passageway of said inner iron tube for passage of said fluid of unknown carbon activity in contact with the walls of said inner tubes.

3. The device of claim 1 wherein said capsule walls consist essentially of iron and said iron oxide layer consists essentially of $Fe_{0.947}O$, said layer being formed by filling said internal chamber with a mixture of CO and $CO_2$ gas to establish the equilibria: $0.947\ Fe + CO \rightleftarrows Fe_{0.947}O + C$ and $1.894\ Fe + CO_2 \rightleftarrows 2\ Fe_{0.947}O + C$ on the internal surfaces of said chamber walls, submersing said capsule in a fluid having a carbon activity sufficiently low to cause carbon from said equilibria to migrate through said capsule walls defining said internal chamber into said fluid and form a layer of $Fe_{0.947}O$ on the surfaces of said walls defining said chamber.

4. The device of claim 3 wherein said layer of $Fe_{0.947}O$ is formed on the internal surfaces of said chamber walls by submersing said capsule in molten sodium metal having a carbon activity of less than $10^{-2}$ at about 700°C. for a period of about 72 hours, said CO and $CO_2$ gas mixture consisting of about 60% CO and 40% $CO_2$ by volume at an initial pressure of 250 Torr, and by subsequently evacuating said chamber while annealing at 700°C for about 15 minutes.

5. A method of measuring the carbon activity of a fluid having unknown carbon activity comprising: forming a layer of iron oxide on the interior wall surfaces defining an internal chamber of a sealed iron capsule; evacuating said chamber; submersing said capsule within said fluid of unknown carbon activity; and measuring the absolute pressure within said capsule internal chamber to determine the carbon activity of said fluid.

6. The method of claim 5 wherein said layer of iron oxide is formed by filling said chamber with about 250 Torr pressure of a gas mixture consisting of approximately 60% CO and 40% $CO_2$, submersing said capsule in a liquid having a carbon activity less than $10^{-2}$; measuring the pressure of said gas mixture while maintaining said capsule submersed in said liquid having a carbon activity of less than $10^{-2}$ until the pressure of said gas mixture decreases to 50 Torr as a result of reacting each of said gases with Fe to form a layer of $Fe_{0.947}O$ and C., withdrawing said capsule from submergence in said liquid, maintaining said capsule at about 700°C. while evacuating residual gas from said internal chamber.

\* \* \* \* \*